United States Patent [19]

Roland

[11] Patent Number: 5,507,299
[45] Date of Patent: Apr. 16, 1996

[54] MULTI-VIAL BLOOD COLLECTION SYSTEM

[76] Inventor: Patricia D. Roland, 4501 Rising Hill Rd., Altadena, Calif. 91001

[21] Appl. No.: 259,325

[22] Filed: Jun. 13, 1994

[51] Int. Cl.⁶ ..................................................... A61B 5/00
[52] U.S. Cl. .......................................... 128/762; 128/760
[58] Field of Search ..................................... 128/760, 762, 128/763, 768; 604/258, 284, 403, 415

[56] References Cited

U.S. PATENT DOCUMENTS

| | | | |
|---|---|---|---|
| 3,405,706 | 10/1968 | Cinqualbre | 128/762 |
| 3,604,410 | 9/1971 | Whitacre | 128/762 |
| 3,696,806 | 10/1972 | Sausse | 128/762 |
| 4,066,067 | 1/1973 | Micheli . | |
| 4,127,111 | 11/1978 | Drolet | 128/760 |
| 4,166,450 | 9/1979 | Abramson . | |
| 4,312,362 | 1/1982 | Kaufman . | |
| 4,326,541 | 4/1982 | Eckels . | |
| 4,327,746 | 5/1982 | Feaster . | |
| 4,333,478 | 6/1982 | Krieg . | |
| 4,409,990 | 10/1983 | Mileikowsky . | |
| 4,412,548 | 11/1983 | Hoch et al. . | |
| 4,418,703 | 12/1983 | Hoch et al. . | |
| 4,436,098 | 3/1984 | Kaufman . | |
| 4,535,786 | 8/1985 | Kater | 128/760 |
| 4,784,157 | 11/1988 | Halls et al. | 128/762 |
| 4,790,330 | 12/1988 | Schwobel et al. . | |
| 4,947,863 | 8/1990 | Haber et al. . | |
| 4,999,307 | 3/1991 | Oakley | 128/762 X |

Primary Examiner—Sam Rimell
Attorney, Agent, or Firm—Willie Krawitz

[57] ABSTRACT

A blood collection system is provided for collecting multiple samples of blood into evacuated vials from a single needle insertion site, and comprises a capillary tube system which acts as a regulator so that samples of blood can be collected at a controlled rate, thereby reducing the risk of vein collapse or other patient trauma. The capillary tube system includes a flexible catheter which mounts an intravenous cannula which can be positioned within a blood vessel from which is drawn the blood sample. A plurality of fittings are located along the length of the capillary tube system, and define openings for interfitting needles, which lie within a series of bores that extend axially from the blood collection system. Samples of blood are taken by inserting covered, evacuated vials into the bores of the blood collection system until a needle pierces the cover of a vial. A blood sample drawn from the patient will flow through the flexible catheter and into the capillary tube system and through the attached needles, and is collected into the multiple evacuated vials, while requiring only a single needle insertion into a patient.

15 Claims, 1 Drawing Sheet

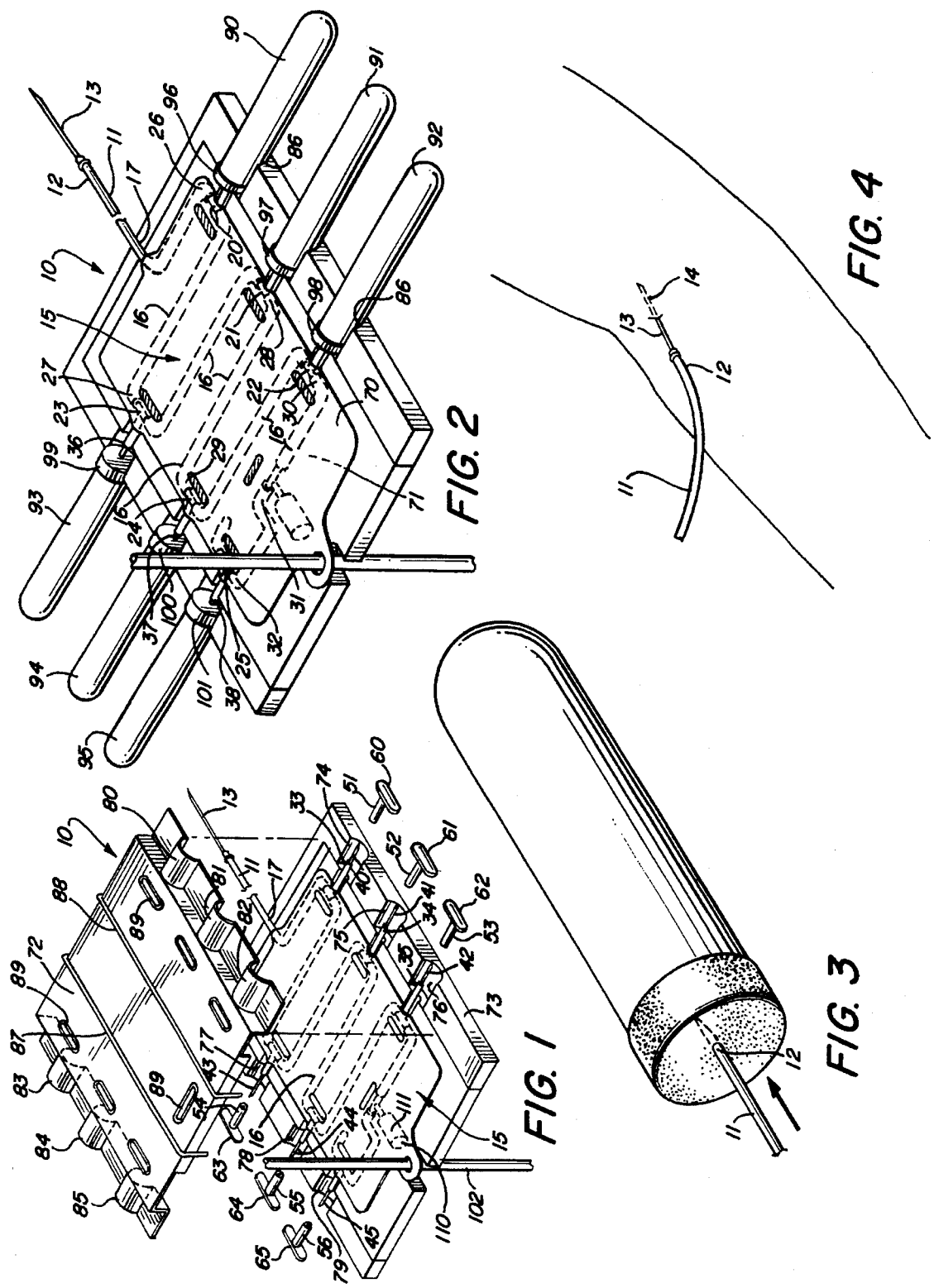

MULTI-VIAL BLOOD COLLECTION SYSTEM

BACKGROUND OF THE INVENTION

This invention relates to a new and improved blood collection system for collecting multiple samples of blood into evacuated tubes from a single needle insertion site.

Various blood collection systems having particular application in vacuum tube phlebotomy are known, and typical prior art devices are shown in U.S. Pat. Nos.: 4,066,067; 4,166,450; 4,312,362; 4,326,541; 4,327,746; 4,333,478; 4,409,990; 4,412,548; 4,418,703; 4,436,098; 4,790,330; and, 4,947,863. Some of these patents describe devices which allow for multiple samples of blood to be collected from a patient in a single procedure, and while these devices provide a means to fill several evacuated blood collection vials, they require removal of a filled vial from a holder before placement and filling of a succeeding evacuated vial can take place. This procedure not only requires frequent and time consuming monitoring of a given patient, but runs the risk of blood leakage particularly during changing of blood collection vials. Furthermore, none of the prior art devices provide a blood collection system where several vials can be filled simultaneously or in succession from a single needle insertion site, without requiring removal of filled vials during the multiple sampling procedure, and only a single needle insertion of the patient.

Also, none of the prior art devices provide a blood collection system where large amounts of blood can be removed from a patient at a controlled rate, while reducing the risk of vein collapse that can occur during rapid blood removal. Moreover, none of the prior art devices provide a blood collection system where the needle insertion site is separated from the blood collection vials in a manner that reduces the risk of prematurely dislodging the needle from the vein. Consequently a need exists for a simple, reliable and disposable blood collection system that can collect large amounts of blood from a single insertion site, while simultaneously distributing the collected blood into one or more evacuated tubes, without leaking blood, or causing patient discomfort or trauma.

Also, it would be helpful if the blood collection system could be easily separated from the filled tubes and subsequently disposed, while reducing the risk of an accidental needle stick, or blood leakage.

THE INVENTION

According to the invention, a blood collection system is provided for collecting multiple samples of blood into evacuated tubes from a single needle insertion site, without requiring removal of filled blood collection tubes during the multiple sampling procedure.

The multiple vial blood collection system comprises a capillary tube system which simultaneously distributes blood into at least one blood collection tube, while acting as a regulator so that samples of blood can be collected at a controlled rate, thereby reducing the risk of vein collapse that can occur during rapid blood removal. The blood sample enters a flexible catheter which mounts an attached cannula positioned within a blood vessel for the purpose of drawing a blood sample, and the blood sample flows through the catheter and cannula and into the capillary tube system.

A plurality of T-shaped fittings are provided along the bends of the capillary tube system, and define openings for a plurality of needles, which lie within a series of bores extending axially from the blood collection system. A blood sample is taken simply by inserting a covered, evacuated vial into a bore of the blood collection system until each needle pierces the cover of a vial. This enables the blood sample to flow from the patient and collected by the vial. Using the blood collection system of this invention, several blood samples can either be taken at separate intervals, in quick succession, or simultaneously.

The vials can be removed from the blood collection system simply by manually withdrawing the filled vials, and when the last blood sample has been taken, the cannula and attached catheter are withdrawn from the patient, and the entire capillary tube system is discarded.

BRIEF DESCRIPTION OF THE DRAWINGS

FIG. 1 is an upper perspective, exploded view of the blood collection system of this invention;

FIG. 2 is an upper perspective view of the capillary tube section of this invention showing a plurality of evacuated vials in place immediately prior to obtaining a blood sample;

FIG. 3 is a perspective view of a needle penetrating the rubber diaphragm of a standard blood collection tube; and, FIG.. 4 shows a placement of an intravenous cannula of the blood collection system in a patient.

DESCRIPTION OF THE PREFERRED EMBODIMENTS

The blood collection system 10, is shown in FIG. 1, 2 and 4, and comprises a flexible catheter 11, whose distal end 12 mounts an intravenous cannula 13 prepositioned within blood vessel site 14. A sinusoidal capillary tube system 15 (shown in dotted designation), containing capillary tube segments 16 is attached to the proximal end 17 of the flexible catheter 11, and functions to collect blood from the single insertion site 14, while simultaneously distributing the blood into one or more evacuated tubes (described, infra), with minimal blood leakage, and reduced patient discomfort or trauma. A typical capillary size may exceed about 1/32" in diameter. A plurality of T-shaped fittings 20–25 are provided along the bends 26–32 of the capillary tube system 15, and define openings 33–38 into which fit a series of needles 40–45 whose cutting edges extend axially from the blood collection system 10. The needles 40–45 are shown attached to a series of needle guards 51–56 by a friction fit, and the needle guards are provided with gripping ends 60–65 that extend axially from the tip of the needles.

As shown in FIGS. 1 and 2, the capillary system 15 is encased between sheets 70 and 71 of transparent plastic film which provide structural support for the capillary tubes and T-shaped fittings 20–25 to prevent or reduce blood leakage. The sheets 70 and 71 of plastic film are in turn secured between a pair of blood protection plates 72 and 73 which provide structural support for the entire blood collection system 10 as well as protection from accidental needle sticks.

FIGS. 1 and 2 show a plurality of curved flanges 74–85 extending axially from the blood protection plates 72 and 73, and the flanges define a series of bores 86 (FIG. 2) which surround the needles 40–45 when the blood protection plates are joined together. A pair of compressor bars 87 and 88 extend over the top of plate 72, and function to inhibit movement of the protection plates when the blood collection system is in use. Alignment holes 89 are defined along the surface of the blood protection plates 72 and 73 and provide a visual means for positioning the blood protection plates prior to application of the compressor bars 87 and 88.

As shown in FIG. 2, and 3, a blood sample is taken simply by inserting evacuated vials 90–95 horizontally into a bore 86 of the blood collection system 10 until the cutting edge of a needle pierces the cover 96–101 of an evacuated vial, thereby causing the blood sample to flow from the blood vessel site 14 through the flexible catheter 11 and into the capillary tube system 15 and collection by evacuated vials 90–95. This enables several blood samples to be taken at separate intervals, in quick succession, or simultaneously.

Regardless of the method of vial insertion, the blood flow is regulated by the length and diameter of the capillary tube segments 16, the pressure differential between the partial vacuum in the evacuated vials 90–95 and the patient's natural blood pressure, and the type of blood vessel site 14 in which the intravenous cannula 13 is placed.

By controlling the rate of blood removal, the risk of vein collapse that can occur during excessively rapid blood removal can be reduced. Also, a medical practitioner can estimate how long it will take for a given volume of blood to be collected from a patient, and distributed to the various evacuated vials. This information can reduce the frequent and time consuming task of monitoring a patient, and free the medical practitioner to collect multiple samples of blood from several patients simultaneously.

After the last blood sample has been taken, the intravenous cannula 13 is withdrawn from the patient, and the filled vials are manually separated from the blood collection system 10. By lifting the compressor bars 87 and 88, and pulling the discard bar 102, the capillary tube system 15 will separate from between the blood protection plates 72 and 73 and is discarded.

It will be appreciated that while the embodiments of this invention are considered to represent the more usual mode of carrying out this invention, many modifications may be made in the size, shape and assembly of the described blood collection system without departing from the basic spirit of the invention. For example, a second similar blood collection system (not shown) can be connected to the disclosed invention by inserting a needle and associated cannula (not shown) horizontally into the cover 110 of end fitting 111, until the cutting edge of a needle (not shown) pierces the cover 110 of end fitting 111, thereby causing additional blood to flow from the blood vessel 14 through the capillary tube system 15 where the blood discharges directly through the secondary catheter and into the capillary tube system of the second blood collection system.

Hence, six additional blood samples can be collected by attaching evacuated vials into the second blood collection system in the same manner as disclosed infra. Also, it may be desired to attach an automated phlebotomy device (not shown) to the end fitting 111 or openings 33–38 to more fully automate the collection of blood and to further reduce the risk of blood contamination. In a similar fashion, an actuator operated hydraulic cylinder (not shown) can be attached to the end fitting 111 or openings 33–38 for the purpose of modifying the flow of blood.

I claim:

1. A blood collection system for simultaneously collecting multiple samples of blood into collection tubes from a single insertion site of a patient including a site insertion needle and connecting catheter, comprising:
   a.) capillary blood collection tubes defining a plurality of capillary tube segments;
   b.) a plurality of fittings connected to the tube segments, for engaging and securing an evacuated blood collection vial;
   c.) a needle extending from each fitting and adapted to engage and pierce a blood collection vial;
   d.) a plastic sheet encasing and providing structural support for the capillary blood collection tubes;
   e.) a site insertion needle and connecting catheter connected to the capillary blood collection tubes; and,
   f.) protection plates for closure and support of the capillary blood collection tubes, the protection plates upon closure defining bores for covering the fittings and needles, and upon opening, the capillary blood collection tubes are removable from between the protection plates; whereby:
   i. when the protection plates are closed and the insertion site of a patient is pierced by the site insertion needle, blood will flow from the site insertion needle and catheter to the capillary tube blood collection system and into a blood collection vial;
   ii. vials filled with blood are removable from the fittings; and,
   iii. the capillary blood collection tubes and extending needles are encased in the plastic sheet, and the site insertion needle and attached catheter are removable from between the protection plates.

2. The blood collection system of claim 1, including blood collection vials connected to the fittings.

3. The blood collection system of claim 1, in which the capillary blood collection tubes regulate the flow of blood at a controlled rate.

4. The blood collection system of claim 1, including compressor bars for closure of the protection plates.

5. The blood collection system of claim 4, in which the capillary blood collection tubes are attached to a discard bar and can be separated from the protection plates by lifting the compressor bars and pulling on a discard bar.

6. The blood collection system of claim 1, comprising an end fitting mounted on the capillary tube system for attaching an automated phlebotomy device or an actuator operated hydraulic cylinder.

7. The blood collection system of claim 1, in which the capillary tube segments have an inside diameter of about at least $1/32$".

8. A method for simultaneously collecting multiple samples of blood into collection tubes from a single insertion site of a patient including a site insertion needle and connecting catheter, the apparatus comprising:
   a.) capillary blood collection tubes defining a plurality of capillary tube segments;
   b.) a plurality of fittings connected to the tube segments, for engaging and securing an evacuated blood collection vial;
   c.) a needle extending from each fitting and adapted to engage and pierce a blood collection vial;
   d.) a plastic sheet encasing and providing structural support for the capillary blood collection tubes;
   e.) a site insertion needle and connecting catheter connected to the capillary blood collection tubes; and,
   f.) protection pirates for closure and support of the capillary blood collection tubes, the protection plates upon closure defining bores for covering the fittings and needles, and upon opening, the capillary blood collection tubes are removable from between the protection plates; the method comprising:
   i. closing the protection plates and piercing the insertion site of a patient by the site insertion needle, whereby blood will flow from the site insertion needle and catheter to the capillary tube blood collection system and into a blood collection vial;

ii. removing vials filled with blood from the fittings; and, iii. removing the capillary blood collection tubes and extending needles encased in the plastic sheet, and removing the site insertion needle and attached catheter from between the protection plates.

9. The method of claim 8, in which several blood samples can be taken in separate intervals, in quick succession, or simultaneously.

10. The method of claim 8, including blood collection vials connected to the fittings.

11. The method of claim 8, in which the capillary blood collection tubes regulate the flow of blood at a controlled rate.

12. The method of claim 8, including compressor bars for closure of the protection plates.

13. The method of claim 12, in which the capillary blood collection tubes are attached to a discard bar and can be separated from the protection plates by lifting the compressor bars and pulling on a discard bar.

14. The method of claim 8, comprising an end fitting mounted on the capillary tube system for attaching an automated phlebotomy device or an actuator operated hydraulic cylinder.

15. The method of claim 8, in which the capillary tube segments have an inside diameter of about at least $\frac{1}{32}$".

* * * * *